US010940158B2

(12) United States Patent
Sangild

(10) Patent No.: US 10,940,158 B2
(45) Date of Patent: *Mar. 9, 2021

(54) COMPOSITIONS FOR USE IN THE PREVENTION OR TREATMENT OF NECROTIZING ENTEROCOLITIS IN INFANTS OR YOUNG CHILDREN BORN BY C-SECTION

(71) Applicant: NESTEC S.A., Vevey (CH)

(72) Inventor: Per Torp Sangild, Copenhagen NV (DK)

(73) Assignee: Societe des Produits Nestle S.A., Vevey (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/036,855

(22) PCT Filed: Nov. 14, 2014

(86) PCT No.: PCT/EP2014/074579
§ 371 (c)(1),
(2) Date: May 16, 2016

(87) PCT Pub. No.: WO2015/071401
PCT Pub. Date: May 21, 2015

(65) Prior Publication Data
US 2016/0296542 A1 Oct. 13, 2016

(30) Foreign Application Priority Data
Nov. 15, 2013 (EP) ..................................... 13193058

(51) Int. Cl.
A61K 31/702 (2006.01)
A23L 33/00 (2016.01)
A23L 33/21 (2016.01)
A23L 33/125 (2016.01)
A23L 33/135 (2016.01)
A61K 35/741 (2015.01)

(52) U.S. Cl.
CPC .......... A61K 31/702 (2013.01); A23L 33/125 (2016.08); A23L 33/135 (2016.08); A23L 33/21 (2016.08); A23L 33/40 (2016.08); A61K 35/741 (2013.01); A23V 2002/00 (2013.01); A23Y 2220/43 (2013.01); A23Y 2220/63 (2013.01); A23Y 2220/73 (2013.01); A23Y 2240/65 (2013.01); A23Y 2300/29 (2013.01); A23Y 2300/45 (2013.01); A23Y 2300/49 (2013.01); A23Y 2300/55 (2013.01)

(58) Field of Classification Search
None
See application file for complete search history.

(56) References Cited

U.S. PATENT DOCUMENTS

| 5,288,637 A | 2/1994 | Roth |
| 2012/0172319 A1 | 7/2012 | Chow et al. |
| 2012/0207882 A1 | 8/2012 | Sonnenburg |

FOREIGN PATENT DOCUMENTS

| EP | 1776877 | | 4/2007 | |
| EP | 1974743 | | 10/2008 | |
| EP | 2454948 | | 5/2012 | |
| EP | 2455387 | | 5/2012 | |
| WO | 9610086 A1 | | 4/1996 | |
| WO | WO 2007/046698 | * | 4/2007 | ............... A23L 1/29 |
| WO | 2009077352 A1 | | 6/2009 | |
| WO | 2013057062 | | 4/2013 | |

OTHER PUBLICATIONS

DeLeoz et al., Journal of Proteome Research, 2012, vol. 11, pp. 4662-4672.*
Thurl et al., British Journal of Nutrition (2010), vol. 104, pp. 1261-1271.*
Asakuma et al., European Journal of Clinical Nutrition (2008) 62, pp. 488-494.*
Weng et al. "The role of gut microbiota in programming the immune phenotype" Journal of Developmental Origin of Health and Disease, 2013, vol. 4, No. 3, pp. 203-214, XP008167952.
Wrodnigg et al., "The Heyns Rearrangement Revisited: An Exceptionally Simple Two-Step Chemical Synthesis of D-Lactosamine from Lactulose", Angew Chem Int Ed Engl., vol. 38, No. 6, Mar. 15, 1999, pp. 827-828.
Gibson et al., "Dietary Modulation of the Human Colonie Microbiota: Introducing the Concept of Prebiotics", The Journal of Nutrition, vol. 125, No. 6, 1995, pp. 1401-1412.
Salminen et al., "Probiotics: how should they be defined?", Trends in Food Science & Technology, vol. 10, No. 3, Mar. 1999, pp. 107-110.
Cilieborg et al. "A Milk Oligosaccharide, 2'-fucosyllactose, May Ameliorate Necrotizing Enterocolitis in Preterm Pigs", Breastfeeding and the Use of Human Milk, Science and Practice, Nov. 9, 2012, 3 pages, XP055536077.

* cited by examiner

Primary Examiner — Scott Long
Assistant Examiner — Evelyn Y Pyla
(74) Attorney, Agent, or Firm — K&L Gates LLP

(57) ABSTRACT

The present invention relates to a composition comprising at least one human milk oligosaccharide and/or a precursor thereof, for use in preventing and/or treating necrotizing enterocolitis in infants or young children born by C-section.

16 Claims, No Drawings

COMPOSITIONS FOR USE IN THE PREVENTION OR TREATMENT OF NECROTIZING ENTEROCOLITIS IN INFANTS OR YOUNG CHILDREN BORN BY C-SECTION

CROSS REFERENCE TO RELATED APPLICATIONS

The present application is a National Stage of International Application No. PCT/EP2014/074579, filed on Nov. 14, 2014, which claims priority to European Patent Application No. 13193058.8, filed Nov. 15, 2013, the entire contents of which are being incorporated herein by reference.

FIELD OF THE INVENTION

This invention relates to compositions to prevent necrotizing enterocolitis in infants or young children who were born by C-section and/or to decrease the duration, the risks, the complications and/or the severity of necrotizing enterocolitis in infants or young children who were born by C-section, and/or to relieve the symptoms caused by necrotizing enterocolitis on health in infants or young children who were born by C-section.

This invention also relates to compositions that can be used for example to promote enteral feeding tolerance and gut functional maturation in infants or young children who were born by C-section.

BACKGROUND OF THE INVENTION

Immaturity of the newborn's gastrointestinal tract functions is a risk factor for inflammatory diseases such as necrotizing enterocolitis or NEC, which is a serious disease of the gastrointestinal tract in neonates. It is associated with several complications like intestinal necrosis that could lead to resection of a part of the intestine, growth and developmental delay, problems of neurodevelopment, such as a long term neurodevelopment impairment, but also with high mortality (up to 20%) and morbidity.

The incidence of the condition is increased with prematurity and low birth weight infants. One reason is the combination of gut functional immaturity and the bacterial colonization of their gut that can easily destabilize the system manifest as enteral feeding intolerance seen as regurgitation and diarrhea and also in severe cases as NEC. Among the igniting factors are the overgrowths of microorganisms such as Enterobacteriacae and coagulase-negative staphylococci. NEC is a complex condition but the action of intestinal flora and gut immaturity are widely established and accepted as pathogenic factors.

Many attempts have been made to prevent NEC in infants. Through prevention of bacterial migration across the mucosa, competitive exclusion of pathogenic bacteria and enhancement of the immune responses of the host, the use of probiotics has been investigated. Gitish Deshpande et al in *Probiotics for prevention of necrotizing enterocolitis in preterm neonates with very low birthweight: a systematic review of randomised controlled trials*, Lancet 2007; 369 (9573) 1614-20, describes that probiotics might reduce the risk of necrotising enterocolitis in preterm neonates with less than 33 weeks' gestation. But it also states that the short-term and long-term safety of probiotics needs to be assessed in large trials and there are unanswered questions such as the dose, duration, and type of probiotic agents used for supplementation. However some other studies on probiotics have not been conclusive, for example Carlo Dani et al, in *Probiotics feedings in prevention of urinary tract infection, bacterial sepsis and necrotizing enterocolitis in preterms infants*, Biol Neonate 2002, 82:103-108, come to the conclusions that seven days of *lactobacillus* GG supplementation starting with the first feed is not effective in reducing the incidence of NEC in preterms infants.

Other pathways have therefore been explored such as the use of oligosaccharides, and especially human milk oligosaccharides. Human milk oligosaccharides (HMOs) are, collectively, the third largest solid constituents in human milk, after lactose and fat. HMOs usually consist of lactose at the reducing end with a carbohydrate core that often contains a fucose or a sialic acid at the non-reducing end. There are approximately one hundred different milk oligosaccharide structures that have been characterized in human milk.

Mother's milk is recommended for all infants. However, in some cases breast feeding is inadequate or unsuccessful for medical reasons or the mother chooses not to breast feed. Infant formulae have been developed for these situations.

Several infant formulae have been developed using HMO ingredients, such as fucosylated oligosaccharides, lacto-N-tetraose, lacto-N-neotetraose, or sialylated oligosaccharides, and for different purposes.

WO2009/077352 relates to a composition suitable in the prevention of opportunistic infections comprising a probiotic *Bifidobacterium* in association with a fucosylated oligosaccharide such as 2'FL. Respiratory, urinary and gastrointestinal tracts infections such as NEC are cited amongst the opportunistic infections that may be prevented.

WO2012/092156 discloses methods for decreasing the incidence of NEC in infants, toddlers or children using human milk oligosaccharides. A very large list of HMOs and precursors thereof is listed in this application, as well as many various combinations of HMOs and precursors thereof, and also many combinations of HMOs with one or several prebiotic oligosaccharides (FOS, GOS, inulin, polydextrose and/or gum). Some probiotics can also be added in the formulations. The possibility of combinations is however very wide in WO2012/092156, which also gives very little guidance regarding the amounts of the HMOs or precursors thereof that should be used to get an efficient result.

WO2012/092156 refers to full-term and premature infants but it is not addressed to infants born by C section.

Infants and young children who were born by C-section have particular needs due to their particular physiological conditions and there is a high risk that these infants and these young children are exposed to diseases such as necrotizing enterocolitis. Immediately before birth, the gastro-intestinal tract of a baby is thought to be sterile. During the normal process of birth via the vaginal delivery, it encounters bacteria from the urogenital and digestive tracts, the skin and the environment of the mother and starts to become colonised. Infants born from C-section therefore do not encounter these bacteria during birth and therefore their microbiota is not properly developed or not adapted. The faecal microbiota of a healthy, vaginally-delivered, breast-fed infant of age 2 to 4 weeks which may be taken as the optimum microbiota for this age group is dominated by *Bifidobacteria* species with some *Lactobacillus* species and lesser amounts of *Bacteroides* such as *Bacteriodes fragilis* species, at the expense of potential pathogens such as Clostridia. After the completion of weaning at about 2 years of age, a pattern of gut microbiota that resembles the adult pattern becomes established.

It should be noted that, in the healthy, vaginally-delivered, breast-fed infant, *Bifidobacteria* form the basis of the microbiota accounting for 60-90% of total bacteria in the infant gut. Breast feeding also promotes intestinal barrier development which, together with bifidobacterial domination leads to enhanced absorption and therefore utilisation of ingested nutrition.

Grönlund et al have studied the faecal microbiota of healthy infants born by caesarean section and compared it with that of a comparable group of infants born by vaginal delivery. They concluded that the gut flora of infants born by caesarean delivery may be disturbed for up to six months after the birth. Specifically they noted that the rates of colonisation by *Bifidobacteria* and *Lactobacilli* in the caesarean group reached the rates of colonisation in the vaginally delivered group only after one month and ten days respectively (Grönlund et al, "Fecal Microflora in Heathy Infants Born by Different Methods of Delivery: Permanent Changes in Intestinal Flora After Cesarean Delivery", Journal of Pediatric Gastroenterology and Nutrition, 28:19-25).

Other workers have suggested that this delayed/aberrant colonisation may have specific consequences in terms of the subsequent development of the infant and have investigated a possible link between these consequences and differences in the gut microbiota. For example, Martino et al investigated colonisation patterns and mucosal IgA production at 6 months of age in relation to early exposures, systemic immune development and early allergic outcomes in a cohort who had received either the probiotic *Lactobacillus acidophilus* strain LAVRI-A1 or a placebo (Martino et al, "Relationship between early intestinal colonisation, mucosal immunoglobulin A production and systemic immune development" Clinical and Experimental Allergy, 38, 69-78).

The proportion of caesarean deliveries continues to increase reaching as much as 70% of all births in some countries. It is therefore clear that there is a need to provide tools to reduce the risk that infants and young children who were born by caesarean section do not suffer adverse health consequences as a result of their mode of delivery. This need is particularly acute given the current practice of routinely administering prophylactic doses of antibiotics to pregnant women who undergo an elective caesarean delivery.

WO 2008/116916 is focused in infants delivered by caesarean section but it is focused on other diseases than necrotizing enterocolitis. It discloses the use of a probiotic strain of *Lactobacillus rhamnosus* and an oligosaccharide mixture in the manufacture of a medicament or therapeutic nutritional composition for reducing the risk of subsequent development of allergy or for preventing or treating diarrhoea in infants delivered by caesarean section.

There is therefore a need to develop compositions suitable for infants or young children who were born by C-section, and especially compositions suitable to prevent and/or to treat necrotizing enterocolitis in infants or young children who were born by C-section and/or suitable to promote enteral feeding tolerance and gastrointestinal functional maturation in infants or young children who were born by C-section, taking into account that the infants or young children born by C-section represent a specific sub-group of patients who have particular physiological conditions and require very specific needs.

There is also a need to deliver such health benefits in a manner that is particularly suitable for these young subjects (infants and young children), in a manner that does not involve a classical pharmaceutical intervention as these infants or young children are particularly fragile.

There is a need to deliver such health benefits in these young subjects in a manner that does not induce side effects and/or in a manner that is easy of deliver, and well accepted by the parents or health care practitioners.

There is also a need to deliver such benefits in a manner that does keep the cost of such delivery reasonable and affordable by most.

SUMMARY OF THE INVENTION

The present inventors have surprisingly found that a composition comprising human milk oligosaccharides is particularly effective for use (i) in promoting enteral feeding tolerance and gastrointestinal functional maturation and (ii) in decreasing the incidence of necrotizing enterocolitis in infants or young children who were born by C-section.

Accordingly, the present invention provides a composition comprising at least one human milk oligosaccharide and/or a precursor thereof, for use in preventing and/or treating necrotizing enterocolitis in infants or young children born by C-section.

The composition according to the invention also allows getting a better gut protection from microbial and pathogen overgrowth, promoting the gut development and maturation, decreasing gut inflammation, promoting the enteral feeding tolerance and/or preventing any diseases and complications associated thereof in infants or young children who were born by C-section.

DETAILED DESCRIPTION OF THE INVENTION

As used herein, the below terms have the following meanings.

The term "infant" means a child under the age of 12 months.

The expression "young child" means a child aged between one and three years, also called toddler.

An "infant or young child born by C-section" means an infant or young child who was delivered by caesarean. It means that the infant or the young child was not vaginally delivered.

A "preterm" or "premature" means an infant or young child who was not born at term. Generally it refers to an infant or a young child born prior 36 weeks of gestation.

The expression "nutritional composition" means a composition which nourishes a subject. This nutritional composition is usually to be taken orally or intravenously, and it usually includes a lipid or fat source and a protein source.

The expression "hypoallergenic nutritional composition" means a nutritional composition which is unlikely to cause allergic reactions.

In a particular embodiment the composition of the present invention is a "synthetic composition". The expression "synthetic composition" means a mixture obtained by chemical and/or biological means, which can be chemically identical to the mixture naturally occurring in mammalian milks (i.e. the synthetic composition is not breast milk).

The expression "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The expression "starter infant formula" means a foodstuff intended for particular nutritional use by infants during the first four months of life.

The expression "follow-on formula" means a foodstuff intended for particular nutritional use by infants aged over four months or by young children and constituting the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The expression "growing-up milk" means a milk-based beverage adapted for the specific nutritional needs of young children.

The expression "fortifier" refers to liquid or solid nutritional compositions suitable for mixing with breast milk or infant formula.

The term "weaning period" means the period during which the mother's milk is substituted by other food in the diet of an infant or a young child.

The expressions "necrotizing enterocolitis" and NEC can be used interchangeably.

The expressions "preventing necrotizing enterocolitis", "preventing NEC" or "prevention of NEC" mean avoiding that NEC occur and/or decreasing the incidence of the NEC (reduction of the frequency, i.e. the number of NEC). It is generally the prevention of NEC occurs during the treatment (i.e. during the administration of the composition of the present invention). It can also encompass the prevention of NEC later in life. The term "later in life" encompasses the effect after the termination of the intervention or treatment. The effect "later in life" can be from 1 week to several months, for example from 2 to 4 weeks, from 2 to 6 weeks, from 2 to 8 weeks, from 1 to 6 months or from 2 to 12 months.

The expressions "treating necrotizing enterocolitis", "treating NEC" or "treatment of NEC" mean decreasing the duration (number of days/weeks/years the infants or young children born by C-section will suffer from NEC), the risks, the complications and/or the severity of necrotizing enterocolitis such as the consequences and the seriousness of NEC (e.g. high mortality and morbidity rates). This also encompasses the relief of the symptoms caused by necrotizing enterocolitis on health and/or the related effects, especially problems of neurodevelopment of infants or young children born by C-section suffering from NEC, such as a long term neurodevelopment impairment, intestinal necrosis that could lead to resection of a part of the intestine, and/or diminishing the pain and/or easing the sleep and/or stabilizing the activity of infants or young children born by C-section suffering from NEC.

By the expression "promoting the enteral feeding tolerance" it is meant a decrease or a suppression of phenomena that may occur during the feeding (due to a feeding intolerance) such as regurgitation, diarrhea, nausea.

The term "HMO" or "HMOs" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "precursor of HMO" is a key compound that intervenes in the manufacture of HMO, such as sialic acid and/or fucose. It is especially a key carbohydrate compound that intervenes in the manufacture of HMO and that is part of the structure of the HMO. In a particular embodiment, the precursor of HMO is chosen from the list consisting of sialic acid, fucose, N-acetyllactosamine (type I or type II) or any mixture thereof. In a specific embodiment, it is sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

A "fucosylated oligosaccharide" is an oligosaccharide having a fucose residue. It has a neutral nature. Some examples are 2-FL (2'-fucosyllactose), 3-FL (3-fucosyllactose), difucosyllactose, lacto-N-fucopentaose I, lacto-N-fucopentaose II, lacto-N-fucopentaose III, lacto-N-fucopentaose V, lacto-N-difucohexaose I, fucosyllacto-N-hexaose, Difucosyllacto-N-hexaose I, Difucosyllacto-N-neohexaose II.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose) and LNnT (lacto-N-neotetraose).

The expression "oligosaccharide mixture" should be understood as a mixture comprising oligosaccharides components, i.e. oligosaccharides such as HMOs, especially sialylated oligosaccharide(s), fucosylated oligosaccharide(s), N-acetylated oligosaccharide(s), but also any precursor thereof. In some embodiments the "oligosaccharide mixture" consists only of (or consists essentially of) HMOs and any precursor thereof.

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999:10 107-10). The microbial cells are generally bacteria or yeasts.

The term "cfu" should be understood as colony-forming unit.

All percentages are by weight unless otherwise stated.

It is noted that the various aspects, features, examples and embodiments described in the present application may be compatible and/or combined together.

In addition, in the context of the invention, the terms "comprising" or "comprises" do not exclude other possible elements.

The present inventors have found that a composition comprising a mixture of human milk oligosaccharides is particularly effective for use in promoting enteral feeding tolerance and gut functional maturation and in decreasing the incidence of necrotizing enterocolitis in infants or young children born by C-section, whereas these infants and young children represent a specific group of subjects requiring particular needs and care.

Infants or young children who were born by C-section have particular needs due to their particular physiological conditions and there is a high risk that these infants or young children are exposed to diseases such as necrotizing enterocolitis. They do not encounter the bacteria from the urogenital and digestive tracts, the skin and the environment of the mother during birth as they are delivered by caesarean and therefore their microbiota is not properly developed or not adapted. Without wishing to be bound by theory, it is believed that a composition comprising at least one human milk oligosaccharide and/or a precursor thereof will increase the mucosal growth in the proximal intestine and/or promote the development of a suitable microbiota, therefore limiting the risks of necrotizing enterocolitis in said infants or young children born by C-section.

An object of the invention is a composition comprising at least one human milk oligosaccharide and/or a precursor thereof, for use in preventing necrotizing enterocolitis in infants or young children born by C-section.

Another object of the invention is a composition comprising at least one human milk oligosaccharide and/or a precursor thereof, for use in treating necrotizing enterocolitis in infants or young children born by C-section, and particularly decreasing the duration, the risks, the complications and/or the severity of necrotizing enterocolitis in infants or young children born by C-section, and/or relieving the symptoms caused by necrotizing enterocolitis on health in infants or young children born by C-section.

Another object of the invention is a composition comprising at least one human milk oligosaccharide and/or a precursor thereof, for use in improving the gut protection from microbial and pathogen overgrowth, in promoting the gut development and maturation, in decreasing gut inflammation, in promoting the enteral feeding tolerance and/or in preventing any diseases and complications associated thereof in infants or young children who were born by C-section. The diseases and complications associated thereof are known by the skilled person. It might be for example diarrhea, growth retardation (i.e. delay in the global size of the infants or young children or delay in the size and/or development of any organ or tissue of said infants or young children) . . . .

In some embodiments the composition of the invention can be used for the different above-mentioned uses in combination, for example the composition can be suitable for use in treating necrotizing enterocolitis, in promoting the gut development and maturation and in promoting the enteral feeding tolerance in infants or young children born by C-section.

More details will now be given regarding the content and the nature of the composition suitable for these different uses.

The composition according to the present invention can comprise one or several human milk oligosaccharide(s) and/or precursor(s) thereof. It can for example comprise one or two or three or four or five or six or seven or even more types of human milk oligosaccharide(s) and/or precursor(s) thereof.

In some embodiments the composition according to the invention comprises at least one human milk oligosaccharide and/or precursor thereof, which is selected from the list comprising N-acetylated oligosaccharide, sialylated oligosaccharide, fucosylated oligosaccharide, sialic acid, fucose and any combination thereof.

In some particular embodiments the composition according to the invention comprises N-acetylated oligosaccharide(s), sialylated oligosaccharide(s), fucosylated oligosaccharide(s), and optionally precursor(s) of human milk oligosaccharide, which are in the following amount (expressed in wt % of the total oligosaccharide mixture):
from 40 to 80 wt % of fucosylated oligosaccharide(s),
from 10 to 50 wt % of N-acetylated oligosaccharide(s),
from 5 to 40 wt % of sialylated oligosaccharide(s), and
from 0 to 20 wt % of precursor(s) of human milk oligosaccharide.

In some particular embodiments the composition according to the invention comprises N-acetylated oligosaccharide(s), sialylated oligosaccharide(s), fucosylated oligosaccharide(s), and optionally precursor(s) of human milk oligosaccharide, which are in the following amount (expressed in wt % of the total oligosaccharide mixture):
from 50 to 70 wt % of fucosylated oligosaccharide(s),
from 20 to 40 wt % of N-acetylated oligosaccharide(s),
from 10 to 30 wt % of sialylated oligosaccharide(s), and
from 0 to 15 wt % of precursor(s) of human milk oligosaccharide.

In some particular embodiments the composition according to the invention comprises N-acetylated oligosaccharide(s), sialylated oligosaccharide(s), fucosylated oligosaccharide(s), and optionally precursor(s) of human milk oligosaccharide, which are in the following amount (expressed in wt % of the total oligosaccharide mixture):
from 60 to 70 wt % of fucosylated oligosaccharide(s),
from 20 to 30 wt % of N-acetylated oligosaccharide(s),
from 10 to 20 wt % of sialylated oligosaccharide(s), and
from 0 to 10 wt % of precursor(s) of human milk oligosaccharide.

The composition according to the invention can comprise N-acetylated oligosaccharide(s). There can be one or several N-acetylated oligosaccharide(s).

The N-acetylated oligosaccharide(s) can be selected from the group comprising lacto-N-tetraose (LNT), lacto-N-neotetraose (LNnT) and any combination thereof.

In some particular embodiments the N-acetylated oligosaccharide is LNT.

In some particular embodiments the N-acetylated oligosaccharide is LNnT.

In some particular embodiments the N-acetylated oligosaccharide is a mixture of LNT and LNnT.

In some particular embodiments the composition comprises both LNT and LNnT in a ratio LNT:LNnT between 5:1 and 1:2, or from 2:1 to 1:1, or from 2:1.2 to 2:1.6.

LNT and LNnT may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999)

Angew. Chem. Int. Ed. 38:827-828. N-acetyl-lactosamine produced in this way may then be transferred to lactose as the acceptor moiety.

In some particular examples of the present invention the total amount of the N-acetylated oligosaccharide(s) can represent from 10 to 50 wt % of the oligosaccharide mixture, or from 15 to 45 wt %, or from 20 to 40 wt %, or from 20 to 35 wt %, or from 20 to 30 wt %, or from 20 to 25 wt % of the oligosaccharide mixture.

The composition according to the invention can contain from 0.1 to 5 g of N-acetylated oligosaccharide(s)/100 g composition on a dry weight basis or from 0.1 to 3 g of N-acetylated oligosaccharide(s)/100 g composition on a dry weight basis.

In particular examples the composition comprises LNT in an amount of from 0.1 to 4, or from 0.3 to 3 or from 0.4 to 2 or from 0.4 to 1, or from 0.4 to 0.9 g/L of composition. In particular examples the composition comprises LNnT in an amount of from 0.1 to 4, or from 0.2 to 2 or from 0.3 to 1.5 or from 0.4 to 1, or from 0.4 to 0.9 g/L of composition In some other embodiments, the composition comprises both LNT and LNnT in these above-mentioned concentrations.

The composition according to the invention can comprise sialylated oligosaccharide(s).

There can be one or several sialylated oligosaccharide(s).

The sialylated oligosaccharide(s) can be selected from the group comprising 3' sialyllactose (3-SL), 6' sialyllactose (6-SL), and any combination thereof.

In some particular embodiments the composition comprises 3-SL and 6-SL.

In some particular embodiments the ratio between 3'-sialyllactose (3-SL) and 6'-sialyllactose (6-SL) can be in the range between 5:1 and 1:10, or from 3:1 and 1:1, or from 1:1 to 1:10.

In some particular embodiments the sialylated oligosaccharide of the composition is 6' sialyllactose (6-SL).

The 3'- and 6'-forms of sialyllactose may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

In some particular examples of the present invention the total amount of the sialylated oligosaccharide(s) can represent from 5 to 40 wt % of the oligosaccharide mixture, or from 5 to 35 wt %, or from 10 to 30 wt %, or from 10 to 25 wt %, or from 10 to 20 wt %, or from 10 to 15 wt % of the oligosaccharide mixture.

The composition according to the invention can contain from 0.05 to 5 g of sialylated oligosaccharide(s), e.g from 0.1 to 2 g, from 0.2 to 1 g of sialylated oligosaccharide(s) per 100 g of composition on a dry weight basis.

In particular examples the composition comprises from 0.05 to 5 g/L of sialylated oligosaccharide(s), or from 0.1 to 4 g/L, or from 0.3 to 2 g/L, or from 0.4 to 1.5 g/L, or from 0.4 to 1 g/L of sialylated oligosaccharide(s), for example 0.5 g/L of sialylated oligosaccharide(s) or 0.9 g/L of sialylated oligosaccharide(s).

In some particular embodiments the composition can also comprise from 0.8 to 1.7 g/l of sialylated oligosaccharide(s).

The composition according to the invention can comprise fucosylated oligosaccharide(s). There can be one or several fucosylated oligosaccharide(s).

For example the fucosylated oligosaccharide can be selected from the group comprising 2'-fucosyllactose (2-FL), 3-fucosyllactose (3-FL), difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyl-lacto-N-neohexaose (such as fucosyllacto-N-neohexaose I, fucosyllacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2' fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

In some particular embodiments the fucosylated oligosaccharide is 2'-fucosyllactose (2-FL).

The fucosylated oligosaccharide may be isolated by chromatography or filtration technology from a natural source such as animal milks. Alternatively, it may be produced by biotechnological means using specific fucosyltransferases and/or fucosydase either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

In the present invention the total amount of the fucosylated oligosaccharide(s) can represent from 40 to 80 wt % of the oligosaccharide mixture, or from 45 to 75 wt %, or from 50 to 70 wt %, or from 55 to 70 wt %, or from 60 to 70 wt %, or from 60 to 65 wt % of the oligosaccharide mixture.

The composition according to the invention can contain from 0.1 to 10 g of fucosylated oligosaccharide, e.g. from 0.1 to 8 g, or from 0.1 to 4 g, or from 0.5 to 3 g of fucosylated oligosaccharide(s) per 100 g of composition on a dry weight basis.

In particular examples the composition comprises from 0.5 to 10 g/L of fucosylated oligosaccharide(s), or from 0.5 to 5 g/L, or from 1 to 4.5 g/L, or from 2 to 4 g/L, or from 2.5 to 3.5 g/L of fucosylated oligosaccharide(s). The amount of fucosylated oligosaccharide(s) will be adapted depending on the needs of the infant or young child. In some examples, the composition can comprise from 0.5 to 2 g/L or from 0.7 to 1.8 g/L of fucosylated oligosaccharide(s). In some other examples, the composition can comprise higher levels of fucosylated oligosaccharide(s) such as from 5 to 10 g/L or from 6 to 8 g/L of fucosylated oligosaccharide(s).

The composition according to the invention can comprise at least one precursor of human milk oligosaccharide.

There can be one or several precursor(s) of human milk oligosaccharide.

For example the precursor of human milk oligosaccharide is sialic acid, fucose or a mixture thereof.

In some particular embodiments the composition comprises sialic acid.

The composition according to the invention can contain from 0 to 2.3 g of precursor(s) of human milk oligosaccharide, e.g from 0 to 1.5 g or from 0 to 0.8 g of precursor(s) of human milk oligosaccharide per 100 g of composition on a dry weight basis.

In particular examples the composition comprises from 0 to 3 g/L of precursor(s) of human milk oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of human milk oligosaccharide.

In some embodiments the composition according to the invention comprises at least one human milk oligosaccharide and/or precursor thereof, which is selected from the list comprising lacto-N-tetraose (LNT), lacto-N-neotetraose (LNnT), 3' sialyllactose (3-SL), 6' sialyllactose (6-SL), 2'-fucosyllactose (2-FL), sialic acid and any combination thereof.

In some embodiments the composition according to the invention comprises at least one human milk oligosaccharide and/or precursor thereof, which is selected from the list comprising lacto-N-tetraose (LNT), lacto-N-neotetraose (LNnT), 6' sialyllactose (6-SL), 2'-fucosyllactose (2-FL), sialic acid and any combination thereof.

In some embodiments the composition according to the invention comprises lacto-N-tetraose (LNT), lacto-N-neotetraose (LNnT), 6' sialyllactose (6-SL), 2'-fucosyllactose (2-FL) and optionally sialic acid.

In some particular embodiments the composition of the present invention comprises 2-FL, LNT, LNnT and 6-SL (for the different uses that are claimed and that can be in the different amounts previously mentioned).

In some particular embodiments the composition of the present invention comprises 2-FL, LNT, LNnT, 6-SL and sialic acid (for the different uses that are claimed and that can be in the different amounts previously mentioned).

In a very specific embodiment, the composition of the present invention comprises N-acetylated oligosaccharide(s), sialylated oligosaccharide(s), fucosylated oligosaccharide(s) and precursor(s) of human milk oligosaccharide, which are in the following amount (expressed in wt % of the total oligosaccharide mixture).

62.8 wt % of fucosylated oligosaccharide(s),
24.1 wt % of N-acetylated oligosaccharide(s),
10.5 wt % of sialylated oligosaccharide(s) and
2.6 wt % of precursor(s) of human milk oligosaccharide.

In a very specific embodiment, the composition of the present invention comprises N-acetylated oligosaccharide(s), sialylated oligosaccharide(s), fucosylated oligosaccharide(s) and precursor(s) of human milk oligosaccharide, which are in the following amount (expressed in wt % of the total oligosaccharide mixture).

62.8 wt % of 2-FL,
10.5 wt % of LNnT,
13.6% of LNT,
10.5 wt % of 6-SL and
2.6 wt % of sialic acid.

In a particular example the composition according to the invention comprises:
from 0.5 to 10 g/L of 2FL
from 0.1 to 4 g/L of LNnT
from 0.1 to 4 g/L of LNT
from 0.1 to 4 g/L of 6SL
from 0 to 2.3 g/L of sialic acid In a particular example the composition according to the invention comprises:
from 2 to 4 g/L of 2FL
from 0.3 to 1.5 g/L of LNnT
from 0.4 to 2 g/L of LNT
from 0.3 to 1 g/L of 6SL
from 0 to 0.8 g/L of sialic acid In a particular example the composition according to the invention comprises:
3 g/L of 2FL
0.5 g/L of LNnT
0.65 g/L of LNT
0.5 g/L of 6SL
0.13 g/L of sialic acid In a particular example the composition according to the invention comprises:
3 g/L of 2FL
0.5 g/L of LNnT
0.65 g/L of LNT
0.5 g/L of 6SL
0 g/L of sialic acid The composition of the invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly *Bifidobacteria* and/or *Lactobacilli*.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM I-1225, *Streptococcus salivarius* DSM 13084 sold by BLIS Technologies Limited of New Zealand under the designation KI2, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The composition according to the invention typically contains from 10e3 to 10e12 cfu of probiotic strain, more preferably between 10e7 and 10e12 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The composition of the invention can further comprise at least one non-digestible oligosaccharide (e.g. prebiotics) other than the human milk oligosaccharides previously mentioned. They are usually in an amount between 0.3 and 10% by weight of composition.

Prebiotics are usually non-digestible in the sense that they are not broken down and absorbed in the stomach or small intestine and thus remain intact when they pass into the colon where they are selectively fermented by the beneficial bacteria. Examples of prebiotics include certain oligosaccharides, such a fructooligosaccharides (FOS) and galactooligosaccharides (GOS). A combination of prebiotics may be used such as 90% GOS with 10% short chain fructo-oligosaccharides such as in the product by BENEO-Orafti sold under the trademark ORAFTI® oligofructose (previously RAFTILOSE®) or 10% inulin such as in the product sold by BENEO-Orafti under the trademark ORAFTI® inulin (previously RAFTILOSE®). A particularly preferred combination of prebiotics is 70% short chain fructo-oligosaccharides and 30% inulin, which is a product sold by BENEO-Orafti under the trademark PREBIO 1.

The composition of the invention can further comprise at least one phage (bacteriophage) or a mixture of phages, preferably directed against pathogenic Streptococci, *Haemophilus, Moraxella* and Staphylococci.

The composition according to the invention can be a nutritional composition, a preparation or a food product.

The composition according to the invention can be for example a nutritional composition such as a synthetic nutritional composition. It can be an infant formula, a starter infant formula, a follow-on formula, a baby food, an infant cereal composition, a growing-up milk, a fortifier such as a human milk fortifier, or a supplement. When the composition is a supplement, it can be provided in the form of unit doses.

In some embodiments the composition of the present invention is typically an infant formula.

The composition of the present invention is typically used in infants or young children who were born by C-section.

These infants and young children represent a specific group of subjects requiring particular needs and care and the present inventors have surprisingly found that a composition comprising at least one human milk oligosaccharides and/or a precursor thereof is particularly effective for use in decreasing the incidence of necrotizing enterocolitis in these infants born by C-section.

The composition according to the invention can be used in term or preterm infants born by C-section.

Advantageously the composition of the invention is for use in preterm infants born by C-section.

In some embodiments the composition of the invention is for use in infants who are small for gestational age and born by C-section.

In some embodiments the composition according to the invention can be for use before and/or during the weaning period.

The human milk oligosaccharide(s) and/or the precursor(s) thereof may be administered in the same composition or they may be administered sequentially.

The composition of the present invention can be in solid (e.g. powder), liquid or gelatinous form.

Since infants born by C-section are especially targeted, the composition could advantageously be a nutritional composition consumed in liquid form.

It may be a nutritionally complete formula such as an infant formula, a starter formula, a follow-on formula or a fortifier such as a human milk fortifier.

The composition according to the invention generally also contains a protein source, preferably in an amount below 2.0 g per 100 kcal, even more preferably in an amount below 1.8 g per 100 kcal. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component peptides or amino acids. The proteins may be either fully or partially hydrolysed. It may be desirable to supply partially hydrolysed proteins (degree of hydrolysis between 2 and 20%), for example for infants and young children believed to be at risk of developing cow's milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In a particular embodiment the composition according to the invention is a hypoallergenic composition. In another particular embodiment the composition according to the invention is a hypoallergenic nutritional composition.

The composition according to the present invention generally contains a carbohydrate source. This is particularly preferable in the case where the nutritional composition of the invention is an infant formula. In this case, any carbohydrate source conventionally found in infant formulae such as lactose, saccharose, maltodextrin, starch and mixtures thereof may be used although the preferred source of carbohydrates is lactose.

The composition according to the present invention generally contains a source of lipids. This is particularly relevant if the nutritional composition of the invention is an infant formula. In this case, the lipid source may be any lipid or fat which is suitable for use in infant formulae. Preferred fat sources include palm oleic, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source preferably has a ratio of n-6 to n-3 fatty acids of about 5:1 to about 15:1; for example about 8:1 to about 10:1.

The composition of the invention also contains preferably all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the composition of the invention may contain emulsifiers and stabilisers such as soy, lecithin, citric acid esters of mono- and di-glycerides, and the like.

The composition of the invention may also contain other substances which may have a beneficial effect such as lactoferrin, nucleotides, nucleosides, and the like.

The composition according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The human milk oligosaccharide(s) and/or precursor(s) thereof will be added at this stage if the final product is to have a liquid form.

If the final product is to be a powder, they may likewise be added at this stage if desired. The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The human milk oligosaccharide(s) and/or the precursor(s) thereof may be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement including the human milk oligosaccharide(s) and/or the precursor(s) thereof in an amount sufficient to achieve the desired effect in an individual. The daily dose of N-acetylated oligosaccharide(s) is typically from 0.1 to 3 g, the daily dose of the sialylated oligosaccharide(s) is typically from 0.1 to 2 g, and the daily dose of the fucosylated oligosaccharide(s) is typically from 0.1 to 4 g.

The amount of oligosaccharides to be included in the supplement will be selected according to the manner in which the supplement is to be administered. For example, if the supplement is to be administered twice a day, each supplement may contain from 0.05 to 1.5 g of N-acetylated oligosaccharide(s), from 0.05 to 1 g of sialylated oligosaccharide(s), and from 0.05 to 2 g of fucosylated oligosaccharide(s).

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The composition can be administered (or given) at an age and for a period that depends on the needs. In some embodiments the composition of the invention is given immediately after birth of the infants by C-section. In some embodiments the composition of the invention is given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first 2 years of life or even more.

In some embodiments, the composition of the invention is given few days, or few weeks, or few months after birth. This may be especially the case when the infant born by C-section is premature, but not necessarily.

The composition of the invention can be given for some days (1, 2, 3, 4, 5, 6 . . . ), or for some weeks (1, 2, 3, 4, 5, 6, 7, 8 or even more), or for some months (1, 2, 3, 4, 5, 6, 7, 8, 9, 10, 11 or even more), or for some years (1, 2 . . . ) depending on the needs.

The composition according to the invention can also allow reducing the hospital stay and the overall health/medical costs.

The present invention also relates to the use of at least one human milk oligosaccharide and/or a precursor thereof, in the preparation of a composition to be administered in infants or young children born by C-section for preventing necrotizing enterocolitis in infants or young children born by C-section and/or for treating necrotizing enterocolitis in infants or young children born by C-section (such as decreasing the duration, the risks, the complications and/or the severity of necrotizing enterocolitis in infants or young children born by C-section, and/or relieving the symptoms caused by necrotizing enterocolitis on health in infants or young children born by C-section).

The present invention also relates to the use of at least one human milk oligosaccharide and/or a precursor thereof, in the preparation of a composition to be administered in infants or young children born by C-section for improving the gut protection from microbial and pathogen overgrowth, for promoting the gut development and maturation, for decreasing gut inflammation, for promoting the enteral feeding tolerance and/or for preventing any diseases and complications associated thereof in infants or young children born by C-section.

The present invention also relates to a method for preventing necrotizing enterocolitis in infants or young children born by C-section and/or for treating necrotizing enterocolitis in infants or young children born by C-section (such as decreasing the duration, the risks, the complications and/or the severity of necrotizing enterocolitis in infants or young children born by C-section, and/or relieving the symptoms caused by necrotizing enterocolitis on health in infants or young children born by C-section), said method comprising administering to said infants or young children born by C-section a composition comprising at least one human milk oligosaccharide and/or a precursor thereof.

The present invention also relates to a method for improving the gut protection from microbial and pathogen overgrowth, for promoting the gut development and maturation, for decreasing gut inflammation, for promoting the enteral feeding tolerance and/or for preventing any diseases and complications associated thereof in infants or young children born by C-section, said method comprising administering to said infants or young children born by C-section a composition comprising at least one human milk oligosaccharide and/or a precursor thereof.

The different embodiments, details and examples previously described in the specification can similarly be applied to these uses and methods.

EXAMPLES

The following examples illustrate some specific embodiments of the composition for use according to the present invention. The examples are given solely for the purpose of illustration and are not to be construed as limitations of the present invention, as many variations thereof are possible without departing from the spirit of the invention.

Example 1

An example of the composition of an infant formula according to the present invention is given in the below table 1. This composition is given by way of illustration only.

TABLE 1 an example of the composition of an infant formula according to the present invention

| Nutrient | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| 2FL (g) | 0.44 | 3 |
| LNT (g) | 0.1 | 0.65 |
| LNnT (g) | 0.08 | 0.5 |
| 6'sialyllactose (g) | 0.08 | 0.5 |

Example 2

Objectives and study:

Human milk oligosaccharides (HMO) may mediate a major part of the known prebiotic and anti-inflammatory effect of human milk in the newborn intestine. Such effects may be particularly important for immature newborns or infants born by C-sections since they are highly sensitive to microbiota- and diet-induced inflammatory conditions. With the aim to show maturational and immunological effects, it will be important to demonstrate effects in a suitable in vivo model showing marked characteristics of gut immaturity and dysregulated immunity. Preterm piglets have recently been well documented to be excellent models of preterm infants, and also to show extreme sensitivity to the beneficial factors in mother's milk. This model allows for detailed manipulations of feeding practices (enteral, parenteral feeding) and show clear clinical manifestations (necrotizing enterocolitis) in response to suboptimal diets.

Method:

For five days after birth, caesarean-delivered preterm pigs were fed increasing doses (3-15 mL/kg/3 h) of a maltodextrin-based enteral milk formula, with (n=17) or without (n=15) the following HMOs mixture (4.78 g/L formula).

TABLE 2 composition of the tested HMOs mixture

| HMO or precursor thereof | Concentration of the HMO or precursor thereof expressed in g/l of the composition | | Amount of the HMO or precursor thereof expressed in wt % of the oligosaccharide mixture | Ratio LNT:LNnT | Type of HMO |
|---|---|---|---|---|---|
| 2FL | 3 | | 62.8 | | neutral |
| LNnT | 0.5 | 1.15 | 10.5 | 1.3 | neutral N-acetylated |
| LNT | 0.65 | | 13.6 | | |
| 6SL | 0.5 | | 10.5 | | charged sialylated |
| Sialic acid | 0.13 | | 2.6 | | |
| Total | 4.78 | | 100 | | |

Clinical conditions, NEC lesions, amount of mucosa and organ weights were recorded on day 5.

Results:

Mean NEC incidence was lower in the HMO group relative to controls (35% vs 53%).

Mucosal weight in the proximal intestine was elevated in the HMO pigs (p<0.05) while body weight, organ weights and diarrhea scores were similar.

Conclusion:

A diet of a HMO-enriched formula according to the invention, given just after birth on caesarean-delivered preterm pigs seems to induce a positive effect on NEC incidence. This formula seems to improve the short-term resistance to necrotizing enterocolitis (NEC) in these pigs that are caesarean-delivered, without involving any apparent adverse effects. Possible explanations could be the increase of mucosal growth in the proximal intestine but also the increase of defense against bacterial pathogens and inflammatory conditions in the newborn intestine which is particularly sensitive and immature when the delivery is made by caesarean since there will be no contact with the mother's flora, and even more sensitive and immature when the subject is premature.

Similar conclusions could be drawn for another experiment made without the addition of sialic acid.

The invention claimed is:

1. A method for treating necrotizing enterocolitis and/or decreasing incidence of necrotizing enterocolitis in an infant or young child born by C-section, the method comprising administering to the infant or young child born by C-section a composition comprising a mixture of human milk oligosaccharides, the mixture comprising 2'-fucosyllactose (2FL) that is 60 to 70 wt. % of the mixture, an N-acetylated oligosaccharide that is 20 to 30 wt. % of the mixture, and 6' sialyllactose (6SL) that is 10 to 20 wt. % of the mixture, the N-acetylated oligosaccharide comprising lacto-N-tetraose (LNT) and lacto-N-neotetraose (LNnT) in a ratio LNT:LNnT between 2:1 and 1:1.

2. The method according to claim 1 wherein the infant or young child is a preterm infant born by C-section, and the composition is administered to the preterm infant born by C-section during the first week after birth of the infant.

3. The method according to claim 1, wherein the mixture further comprises a precursor of human milk oligosaccharide selected from the group consisting of sialic acid, fucose and combinations thereof.

4. The method according to claim 1 wherein the composition is administered in an amount that provides a daily dose of 0.1 to 3 g of the N-acetylated oligosaccharide.

5. The method according to claim 1 wherein the composition is administered in an amount that provides a daily dose of 0.1 to 2 g of the 6' sialyllactose (6SL).

6. The method according to claim 1 wherein the composition is administered in an amount that provides a daily dose of 0.1 to 4 g of the 2'-fucosyllactose (2FL).

7. The method according to claim 1, wherein the mixture further comprises 3' sialyllactose (3-SL).

8. The method according to claim 1, wherein the mixture further comprises a fucosylated oligosaccharide selected from the group consisting of 3-fucosyllactose (3-FL), difucosyllactose, lacto-N-fucopentaose I, lacto-N-fucopentaose II, lacto-N-fucopentaose III, lacto-N-fucopentaose V, lacto-N-difucohexaose I, lacto-N-fucohexaose, fucosyllacto-N-hexaose, fucosyllacto-N-neohexaose, difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and combinations thereof.

9. The method according to claim 1 wherein the mixture further comprises sialic acid.

10. The method according to claim 1, wherein the composition comprises at least one probiotic in an amount of from $10^3$ to $10^{12}$ cfu/g of the composition (dry weight).

11. The method according to claim 1, wherein the composition is selected from the group consisting of a nutritional composition, a preparation and a food product.

12. The method according to claim 1, wherein the composition is selected from the group consisting of an infant formula, a starter infant formula, a follow-on infant formula, a baby food, an infant cereal composition, a growing-up milk, a fortifier and a supplement.

13. The method according to claim 1, wherein the composition is administered to the infant or young child before and/or during the weaning period.

14. The method according to claim 1, wherein the infant or young child is a preterm infant born by C-section.

15. The method according to claim 1, wherein the N-acetylated oligosaccharide comprises lacto-N-tetraose (LNT) and lacto-N-neotetraose (LNnT) in a ratio LNT:LNnT between 2:1.2 and 2:1.6.

16. The method according to claim 1, wherein the N-acetylated oligosaccharide comprises lacto-N-tetraose (LNT) and lacto-N-neotetraose (LNnT) in a ratio LNT:LNnT of 1.3:1.

* * * * *